(12) United States Patent
Hong et al.

(10) Patent No.: US 9,295,431 B2
(45) Date of Patent: Mar. 29, 2016

(54) CONSTRUCTING A 3-DIMENSIONAL IMAGE FROM A 2-DIMENSIONAL IMAGE AND COMPRESSING A 3-DIMENSIONAL IMAGE TO A 2-DIMENSIONAL IMAGE

(71) Applicant: New York University, New York, NY (US)

(72) Inventors: Kyonsoo Hong, New York, NY (US); Makoto Nishiyama, New York, NY (US); Kazunobu Togashi, Isezaki (JP)

(73) Assignee: New York University, New York, NY (US)

( * ) Notice: Subject to any disclaimer, the term of this patent is extended or adjusted under 35 U.S.C. 154(b) by 488 days.

(21) Appl. No.: 13/661,695

(22) Filed: Oct. 26, 2012

(65) Prior Publication Data

US 2013/0107007 A1    May 2, 2013

Related U.S. Application Data

(63) Continuation-in-part of application No. 13/660,829, filed on Oct. 25, 2012.

(60) Provisional application No. 61/553,020, filed on Oct. 28, 2011.

(51) Int. Cl.
*G06T 7/00* (2006.01)
*H04N 13/04* (2006.01)
*A61B 6/00* (2006.01)

(52) U.S. Cl.
CPC ............... *A61B 6/00* (2013.01); *G06T 7/0069* (2013.01); *G06T 2207/10004* (2013.01); *H04N 13/0495* (2013.01)

(58) Field of Classification Search
None
See application file for complete search history.

(56) References Cited

U.S. PATENT DOCUMENTS

| | | | | |
|---|---|---|---|---|
| 2003/0228053 | A1* | 12/2003 | Li et al. | 382/154 |
| 2005/0265590 | A1* | 12/2005 | Li et al. | 382/131 |
| 2008/0219535 | A1* | 9/2008 | Mistretta et al. | 382/131 |
| 2010/0084555 | A1* | 4/2010 | Luo et al. | 250/311 |
| 2011/0007072 | A1* | 1/2011 | Khan et al. | 345/420 |
| 2011/0164124 | A1* | 7/2011 | Hizume et al. | 348/61 |
| 2011/0194787 | A1* | 8/2011 | Chun et al. | 382/284 |

OTHER PUBLICATIONS

Hong, Kyonsoo, et al., A Ligand-Gated Association between Cytoplasmic Domains of UNC5 and DCC Family Receptors Converts Netrin-Induced Growth Cone Attraction to Repulsion, Cell, vol. 97, 927-941, Jun. 25, 1999, U.S.A., pp. 927-941.

Hong, Kyonsoo, et al., Calcium signalling in the guidance of nerve growth by netrin-1, Nature/vol. 403/Jan. 6, 2000/www.nature.com, 2000 Macmillan Magazines, Ltd., U.S.A., pp. 93-98.

(Continued)

*Primary Examiner* — Jay Patel
*Assistant Examiner* — Reza Aghevli
(74) *Attorney, Agent, or Firm* — Foley & Lardner LLP

(57) ABSTRACT

Systems and methods for receiving a blurred two-dimensional image captured using an optic system. The blurred two-dimensional image is deconvoluted using a point spread function for the optic system. A stack of non-blurred two-dimensional images is generated, each non-blurred image having a z-axis coordinate. A three-dimensional image is constructed from the stack of two-dimensional images.

20 Claims, 8 Drawing Sheets

(56) References Cited

OTHER PUBLICATIONS

Nishiyama, Makoto, et al., Calcium stores regulate the polarity and input specificity of synaptic modification, Letters to Nature, Nature/vol. 408/Nov. 30, 2000/www.nature.com, 2000 Macmillan Magazines Ltd., pp. 584-588.

Nishiyama, Makoto, et al., Cyclic AMP/GMP-dependent modulation of $Ca^{2+}$ channels sets the polarity of nerve growth-cone turning, Letters to Nature, Natur/vol. 423/Jun. 26, 2003/www.nature.com/nature, 2003 Nature Publishing Group, U.S.A., pp. 990-995.

Li, Weiquan, et al., Activation of FAK and Src and receptor-proximal events required for netrin signaling, Nature Neuroscience vol. 7/No. 11/Nov. 2004, 2004 Nature Publishing Group, Inc. http://www.nature.com/natureneuroscience, U.S.A., pp. 1213-1221.

Nishiyama, Makoto, et al., Membrane potential shifts caused by diffusible guidance signals direct growth-cone turning, Nature Neuroscience, vol. 11, No. 7, Jul. 2008, 2008 Nature Publishing Group, http://www.nature.com/natureneuroscience, pp. 762-771.

Togashi, Kazunobu, Cyclic GMP-Gated CNG Channels Function in Sema3A-Induced Growth Cone Repulsion, Cell Press, Neuron 58, 694-707, Jun. 12, 2008.

Hong, Kyonsoo, et al., From Guidance Signals to Movement: Signaling Molecules Governing Growth Cone Turning, The Neuroscientist, vol. 16, No. 1, Feb. 2010, pp. 65-78.

Nishiyama, Makoto, et al., Semaphorin 3A induces $Ca_v2.3$ channel-dependent conversion of axons to dendrites, Nature Cell Biology, vol. 13, No. 6, Jun. 2011, pp. 676-686.

Hong, Kyonsoo, et al., A transmembrane domain of the putative channel subunit MEC-4 influences mechanotransduction and neurodegeneration in C. elegans, Nature, vol. 367, Feb. 3, 1994, U.S.A., pp. 470-473.

Yamashiro, Shigeko, Characterization of the COOH Terminus of Non-muscle Caldesmon Mutants Lacking Mitosis-specific Phosphorylation Sites, The Journal of Biological Chemistry, vol. 270, No. 8, Issue of Feb. 24, 1995, U.S.A., pp. 4023-4030.

Lai, C.C., et al., Sequence and Transmembrane Topology of MEC-4, an Ion Channel Subunit Required for Mechanotransduction in Caenorhabditis elegans, The Rockefeller University Press, 0021-9525/96/06/1071/11, The Journal of Cell Biology, vol. 133, No. 5, Jun. 1996 1071-1081, U.S.A., pp. 1071-1081.

Hong, Kyonsoo, In Vivo Structure-Function Analyses of Caenorhabaditis elegans MEC-4, a Candidate Mechanosensory Ion Channel Subunit, The Journal of Neuroscience, Apr. 1, 2000, 20(7):2575-2588, U.S.A., pp. 2575-2588.

Nishiyama, Makoto, GABAergic activities control spike timing- and frequency- dependent long-term depression at hippocampal excitatory synapses, Frontiers in Synaptic Neuroscience, Jun. 23, 2010, vol. 2, Article 22, www.frontiersin.org, pp. 1-15.

Nishiyama, Makoto, et al., Localization of Arachidonate 12-Lipoxygenase in Canine Brain Tissues, Journal of Neurochemistry, vol. 58, No. 4, 1992 International Society of Neurochemistry, pp. 1395-1400.

Nishiyama, Makoto., et al., Arachidonate 12-Liposygenase is Localized in Neurons, Glial Cells, and Endothelial Cells of the Canine Brain, Journal of Histochemistry & Cytochemistry, vol. 41, No. 1, 1993, U.S.A., pp. 111-117.

Nishiyama, Makoto, et al., Endothelium is required for 12-hydroperoxyeicosatetraenoic acid-induced vasoconstriction, European Journal of Pharmacology 341 (1998) 57-63, pp. 57-63.

Nishiyama, Makoto, et al., Potassium channels activated in the endothelium-dependent hyperpolarization in guinea-pig coronary artery, Journal of Physiology (1998), 510.2, pp. 455-465.

Yajima, Kazuhiro, et al., Inhibition of endothelium-dependent hyperpolarization by endothelial prostanoids in guinea-pig coronary artery, British Journal of Pharmacology (1999) 126, 1-10, United Kingdom, pp. 1-10.

Okamoto, Hisayo, et al., Role of 12-Hpete in the Pathogenesis of Cerebal Vasospasm, Eicosanoids and Other Bioactive Lipids in Cancer Inflammation and Radiation Injury 3, Plenum Press, New York, 1997, U.S.A., pp. 21-25.

Yamashiro, Shigeko, Caldesmon: Possible Functions in Microfilament Re-Organization During Mitosis and Cell Transformation, Actin: Biophysics, Biochemistry, and Cell Biology, Plenum Press, New York, 1994, U.S.A., pp. 113-122.

US Office Action for U.S. Appl. No. 13/660,829 mailed Feb. 5, 2015, 17 pages.

\* cited by examiner

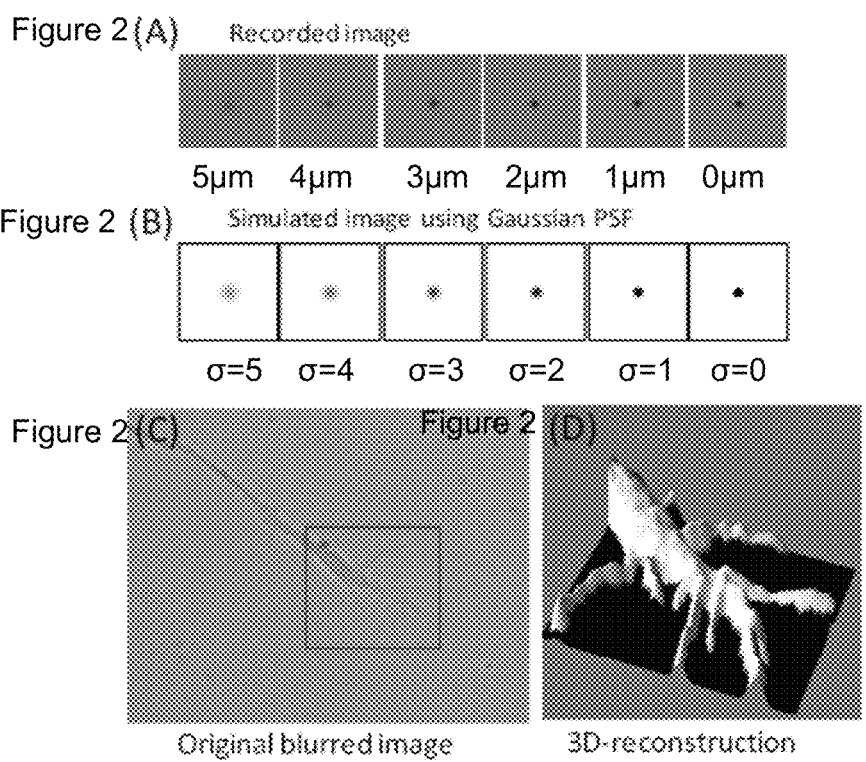

Figure 3A         Figure 3B         Figure 3C
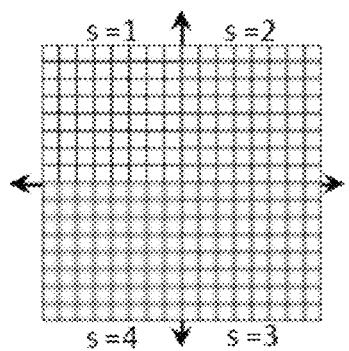 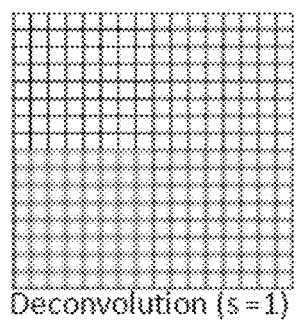 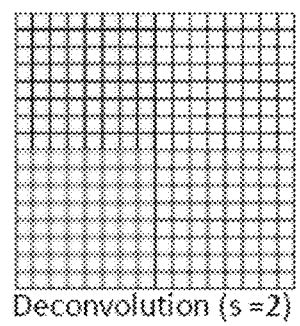
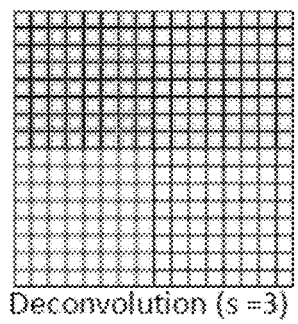 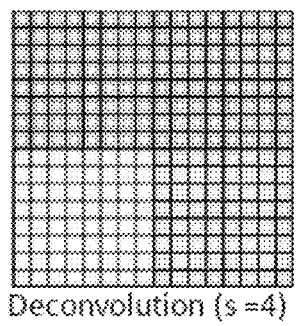 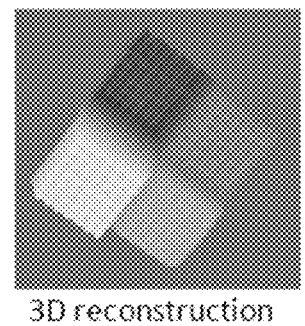
Figure 3D         Figure 3E         Figure 3F Figure 5A PSF from recording
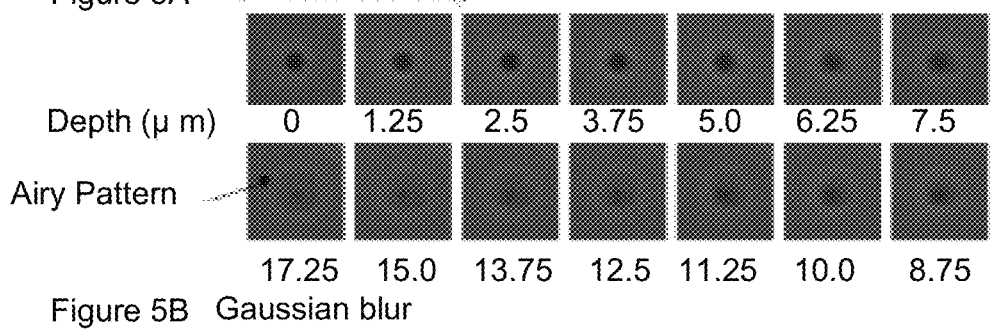
Depth (μ m)  0   1.25  2.5  3.75  5.0  6.25  7.5
Airy Pattern
17.25  15.0  13.75  12.5  11.25  10.0  8.75
Figure 5B Gaussian blur
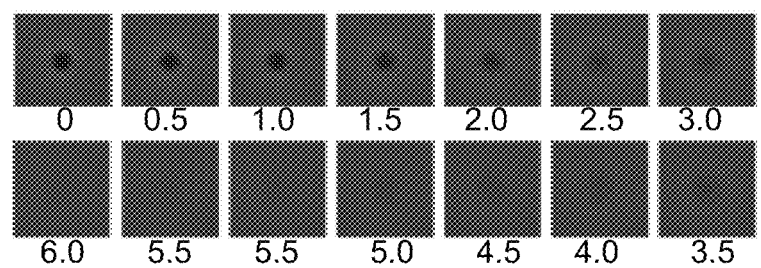
0   0.5   1.0   1.5   2.0   2.5   3.0
6.0   5.5   5.5   5.0   4.5   4.0   3.5

CONSTRUCTING A 3-DIMENSIONAL IMAGE FROM A 2-DIMENSIONAL IMAGE AND COMPRESSING A 3-DIMENSIONAL IMAGE TO A 2-DIMENSIONAL IMAGE

CROSS-REFERENCE TO RELATED APPLICATIONS

This application is a continuation in part of U.S. application Ser. No. 13/660,829, filed Oct. 25, 2012, which claims the benefit of U.S. Provisional Application No. 61/553,020, filed Oct. 28, 2011, each of which is incorporated by reference herein in its entirety.

GOVERNMENT RIGHTS

This invention was made with government support under grant NS064671 awarded by the National Institutes of Health. The government has certain rights in the invention.

BACKGROUND OF THE INVENTION

Three-dimensional images provide valuable information in an increasing number of situations. For example, long-term monitoring of the localization and activity of signaling molecules in cells together with changes in cell morphology is a power experimental method to assess the normal cellular internal state or the state during various pathological disorders. Currently, a majority of works investigating three-dimensional distributions of signaling molecules and morphological changes almost exclusively rely on construction of the three-dimensional image from z-series of multiple (normally >30) two-dimensional images. To do this, researchers are normally required to acquire z-series (depth/height axis) images of experimental samples using a confocal or two-photon microscopy. For example, a series of images may be captured of the same x-y area, each image being at a different distance from the subject of the image and having a different focal plane. Each of the z-series images has in-focus portions and out-of-focus portions. Known deblurring algorithms are then typically applied to each image to remove the out-of-focus portions for that image. Assembly of the resultant, in-focus z-series images results in a three dimensional image. This process is costly and time consuming. Most importantly in many applications, the acquisition of z-series images is inevitable to encounter the problems due to photo-toxicity and photo-bleaching, and would not be capable to detect faster spatio-temporal dynamics of signaling molecules and morphology changes.

SUMMARY OF THE INVENTION

One embodiment relates to methods for generating a three-dimensional image, comprising receiving a blurred two-dimensional image. The two-dimensional image is deconvoluted using a point spread function for the optic system that captured the blurred two-dimensional image. A stack of deconvoluted two-dimensional images is generated, each non-blurred image having a z-axis coordinate. From the stack of two-dimensional images a three-dimensional image is constructed.

In another embodiment, the invention relates to methods for generating a blurred two-dimensional image. A three-dimensional image is received. The three-dimensional image is deconstructed into a series of two-dimensional images each having a corresponding z-axis coordinate. Each of the two-dimensional images is convoluted using a point spread function associated with the z-axis coordinate. A single blurred two-dimensional image is generated corresponding with an approximated focal plane of the optic system.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIGS. 2A-D illustrate images corresponding to one embodiment of the steps set forth in the flow chart of FIG. 1.

FIGS. 3A-F illustrate an artificial two-dimensional blurred image having 4 discrete areas of blur demonstrating principles of the present invention; FIG. 3A illustrates the two-dimensional blurred image; FIG. 3B illustrates the image deconvoluted with SD=1 (s=1) from FIG. 3A; FIG. 3C illustrates the image deconvoluted with SD=2 (s=2) from FIG. 3A; FIG. 3D illustrates the image deconvoluted with SD=3 (s=3) from FIG. 3A; FIG. 3E illustrates the image deconvoluted with SD=4 (s=4) from FIG. 3A; and FIG. 3F illustrates a three-dimensional reconstruction of the blurred two-dimensional image of FIG. 3A following deconvolution.

FIG. 4A (A), is the original, blurred two-dimensional growth cone image. FIG. 4B (A'), is a three-dimensional reconstructed growth cone image from a single, blurred two-dimensional image. The blurred Mermaid fluorescence signal is tentatively transformed.

FIG. 5 illustrates differences between recorded point source image (in-focus as a depth is 0) and its out-of focus images with corresponding depths (FIG. 5A) and point source images filtered with given grades (SD) of Gaussian blurs (FIG. 5B) used to estimate depth of objects.

DETAILED DESCRIPTION OF THE PREFERRED EMBODIMENTS

Figure 1:
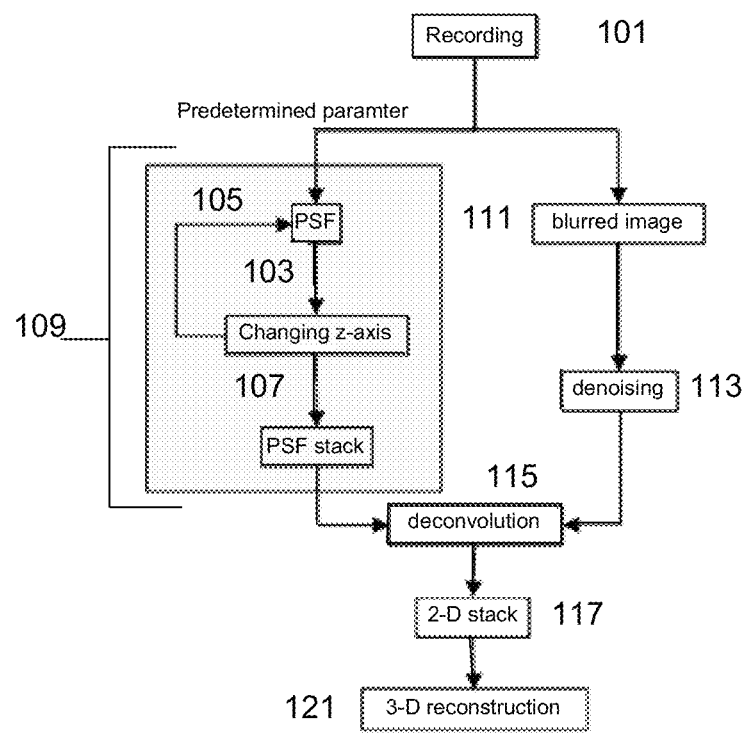
FIG. 1 is a flow chart illustrating a procedure of reconstructing a three-dimensional image from a single, blurred two-dimensional image.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

In one embodiment, system and methods are provided to convert two-dimensional data into three-dimensional data. For example, systems and methods of the present invention may be used to construct three-dimensional images from a single two-dimensional image. Some methods of the present invention extract a z-axis registry from blurred images (i.e., decoding of z-axis registry) using the magnitude of blur at given xy-registry, which correlates with the deviation of the z-axis from the focal plane. The term blurred image is used to refer to an image that may have a portion blurred, not, necessary, that the entire image is blurred. This derivation along z-axis can be mathematically calculated based on a point-spread function (PSF) of the optics used to capture the two dimensional image. The PSF is calculated for the optics used in a given application, such as the particular microscope used, by comparing the blurred images to computationally generated blur, such as Gaussian blur.

FIG. 1 illustrates a flow chart depicting a method of generating a three-dimensional image from a two-dimensional image. A two-dimensional image is obtained/recorded, 101. This image may contain in-focus and out-of-focus portions. First, the z-axis must be indexed to correlate blur with the z-axis dimension, 109, as shown in the box in FIG. 1. To measure PSF, capture images of an object, such as a bead, are captured under the optics, such as a microscope, 103. The z-axis, i.e. focal level, is changed, 105. This process of changing the z-axis position and capturing an image is repeated. Thus, while moving the focal levels along the z-axis in steps, a z-series of blurred images of the object are captured, 105. In various implementations, the size of each step is between 0.5 and 1.5 μm. It should be appreciated, the blurred images may be provided by an optical system, with the necessary metadata to determine the z-stack, to another system that generates the three-dimensional image. A series of blurred (defocused) images with various standard deviation ("SD" or σ) are computationally constructed from the best focused image that was obtained experimentally, 107. Best fit parameters to minimize mean square error between recorded blurred images and constructed images with Gaussian blurs or blur functions specific to given objectives are applied to provide depth estimation for a given blur. In one embodiment, the data are for taste and smell rather than a visual image. For example, for taste and smell, molecular diffusion is measured via two dimensions with the third dimension being neuronal spike coding (replacing z axis by t: time frame). For embodiments where the data is not an image, axis referred to above may be correlated to an appropriate aspect. For example, t-axis (time domain) (depending on the frame rate of image capturing) can be encoded by filtering function other than PSF. Alternatively, for movie files, brain mapping can be encoded for x-y axis and each frame can represent t-axis.

FIGS. 5A and 5B illustrates differences between another series of recorded images at varying depth (z-axis) (FIG. 5A) and the simulated Gaussian blur (FIG. 5B) used to estimate depth of objects. FIGS. 5A and 5B illustrate a further example of implementing the PSF calculation 109 of the flow chart in FIG. 1.

Figure 6:
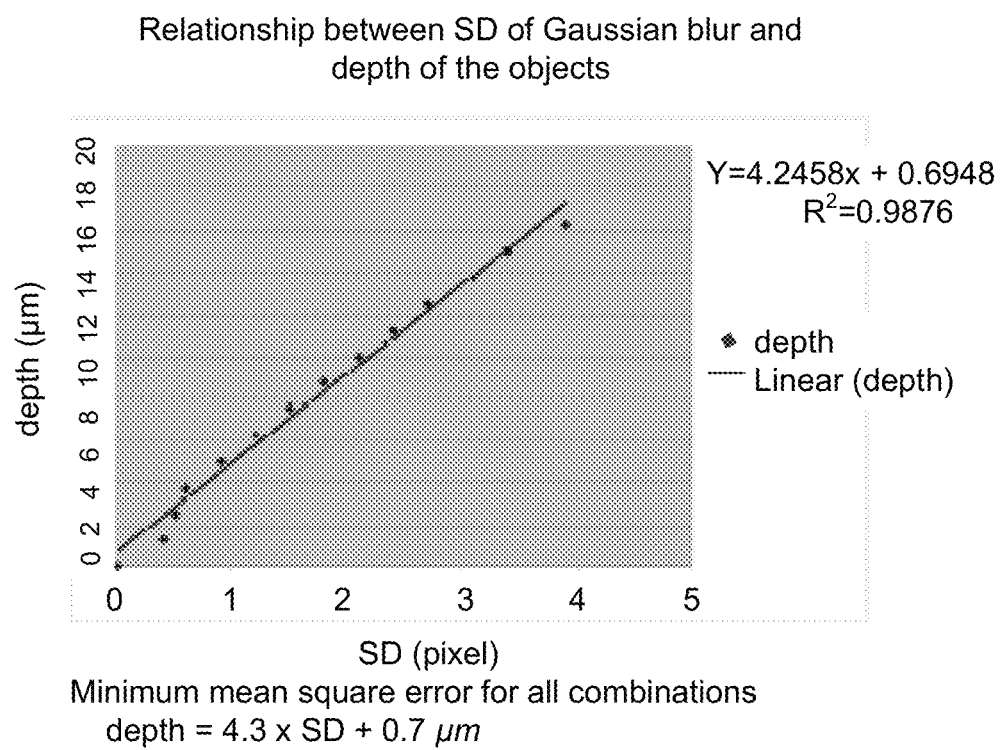
FIG. 6 is a graph illustrating the relationship between SD of Gaussian blur and depth of the corresponding object.

FIG. 6 is a graph illustrating the relationship between SD of Gaussian blur and depth of the corresponding object shown in FIGS. 5A and 5B. The depth estimates is determined by best fit parameters to minimize a mean square error between recorded blurred images (FIG. 5A) and constructed images with Gaussian blurs (FIG. 5B). The chart of FIG. 6 shows the relationship between SD (σ) of Gaussian blurs and the depth of the objects when mean square error is minimized.

Once the parameters for depth assessment by PSF are determined (109), the blurred image 111 recorded is denoised, 113. The denoised blurred image is then processed with deconvolution filtering, 115, according to the PSF to generate a stack of deblurred two-dimensional images, 117. A three-dimensional image is reconstructed from the deblurred two-dimensional image, 121.

FIGS. 3A-F depicts the general principle of the method of FIG. 1 to reconstruct three-dimensional views from two-dimensional views. A square consists of four quarters with different degrees of Gaussian blur (from σ=1 to σ=4). While applying different magnitudes of deconvolution filtering (from σ=1, FIG. 3B to σ=4, FIG. 3E) required to deblur the two-dimensional view, each focused quarter area can be determined, e.g., deconvolution (σ=1) for the top left quarter, deconvolution (σ=2) for the top right quarter, etc. From the degrees of deconvolution filtering required to deblur each area, we are able to assess how far out of focus the original area was along the z-axis. By knowing the relationship between the deconvolution necessary to deblur and the relationship between deblurring, for the optical system that took the image, and position along the z-axis, a three-dimensional view can be reconstructed from this information. FIG. 3F illustrates a three-dimensional view generated from the blurred image of FIG. 3A.

In one embodiment the systems and methods of the present invention may be utilized with epi-fluorescence microscopy. Three-dimensional views of signaling events and cellular morphology can be reconstructed from single, blurred two-dimensional images. A conventional epi-fluorescence microscope may be used to capture blurred two-dimensional images instead of more costly confocal and/or two-photon microscopes. Importantly, the method of three-dimensional microscopy of the present invention does not require capture of z-series images for the three-dimensional reconstruction, thereby avoiding photo-toxicity of living sample and fluorochrome photo-bleaching, making long-term measurements feasible. In one embodiment, the systems and methods herein may be used to monitor three-dimensional neurite trajectories in whole *Xenopus* spinal cords in vivo (approximately 150 μm×1,500 μm×150 μm). In further embodiments, the systems and methods are also be applicable to microscopic imaging of other typical experimental organisms such as *C. elegans, Drosophila* and *Zebrafish*, mutant strains of which mimic various neurological disorders.

It should be appreciated that in some applications it is very difficult to distinguish between out of focus signals at the near side from those at far side of the focal plane if the distances from the focal plan are equal using current, deconvolution image processing. For this reason, in certain embodiments a z-axis reference, such as fluorescent beads, is used during image acquisition in vivo. Further, an edge-detection algorithm may be incorporated into the described deconvolution image processing systems and methods. In one embodiment, the edge detection algorithm is configured to detect a target tissue, such as for in vivo applications of embodiments of the present invention for microscopy. In one embodiment, epifluorescent microscope imaging systems in accordance with the present invention are capable of visualizing fluorescent signals emitted from a depth of up to about 100 μm.

In one embodiment, a system of the present invention can simultaneously monitor three-dimensional florescence resonance energy transfer ("FRET") signals and cellular morphology. An imaging system for such an application may use an upright/inverted hybrid microscope with two EMCCD cameras, in which the focal level between the upright and inverted objectives are set at about 20 µm, as optimized by computational modeling. This system will allow not only simultaneous monitoring of FRET signals and morphology at a distance of ca. 60 µm along a z-axis from two mirror two-dimensional images, but also the application of Bayesian superresolution algorithms that will increase the spatial resolution at a 2 square root order. Multi-line laser excitation may also be used.

Some examples set forth herein are described in the context of fluorescence microscopy. However, it should be appreciated that the principles of the present invention may be applied in other applications. Other applications include merging/compression of multiple data/information of different modalities/characters into single file format, thereby facilitating a data transfer and accelerating data/information processing. For example, the methods described herein could be used to convert a three-dimensional image. The three-dimensional image is deconstructed/disassembled to form a single two-dimensional image having a z-coordinate information/registry as blurs. The two-dimensional image is then convoluted to reduce the stack of two-dimensional images to a single two-dimensional image with blurred portions. In one embodiment, the convolution utilizes best fit parameters to determine the two-dimensional image of the stack of two-dimensional images that is least blurred, i.e. closest to the focal plane, and the remaining images are convoluted with respect position along the z-axis relative to that least blurred image of the stack. In certain embodiments, the systems and methods described herein can encode sensation information, such as visual, auditory, gustatory, olfactory, and tactile. Olfactory, taste and tactile may be encoded using neuronal spike coding observed in nervous system corresponding to these sensations. In one embodiment, multi-modal information can be stored or registered in the same file using the present invention. For example, looking at movies such as someone is eating an apple, you can smell and taste an apple, although additional devices to stimulate your brain are needed for such application.

In one embodiment; systems and methods of the present invention may be used to convert a three-dimensional image to a blurred two-dimensional image. It should be appreciated, three-dimensional data may be converted to a blurred two-dimensional data as a compression mechanism to facilitate efficient transmission of three-dimensional data.

EXAMPLES

The image processing according to the flow chart depicted in FIG. 1 was applied to fluorescence microscopy. First, the point spread function (PSF) of the optics, an upright epi-fluorescence microscope (Olympus BX-51WI) with a water-immersion objective (Olympus LUMFLN 60XW, N.A. 1.1), where measured, 101. The PSF is determined by capturing images of fluorescent beads (ca. 1 µm) with various degrees of blur by changing the microscope z-axis and aperture stop by closing the iris or applying a pinhole light pass (105 in FIG. 1). FIG. 2A illustrates the series of images experimentally captured. In addition, Gaussian blurred images were generated computationally (107 in FIG. 1). FIG. 2B illustrates the series of images computationally generated. By comparing the images of FIGS. 2A and B, the deviation of the bead from the focal point along z-axis is estimated based on the PSF of the optics.

Figure 4A:
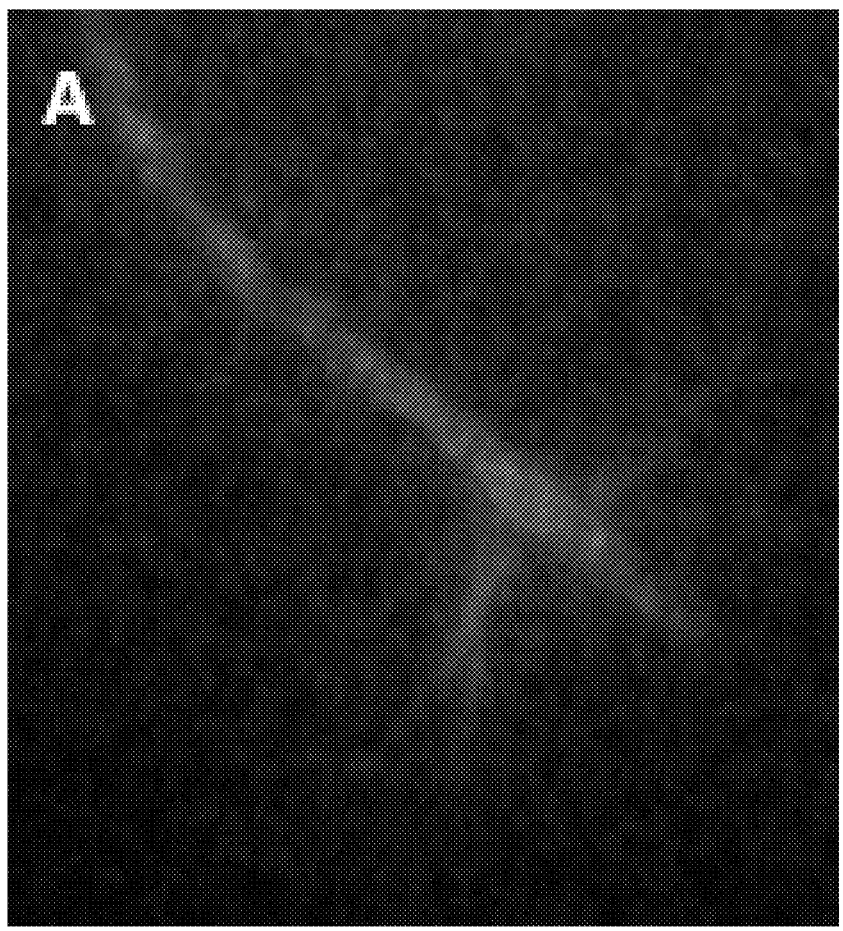
FIGS. 4A and 4B are a three-dimensional reconstruction of a growth cone of a spinal neuron expressing the voltage-sensing Mermaid protein.
Figure 4B:
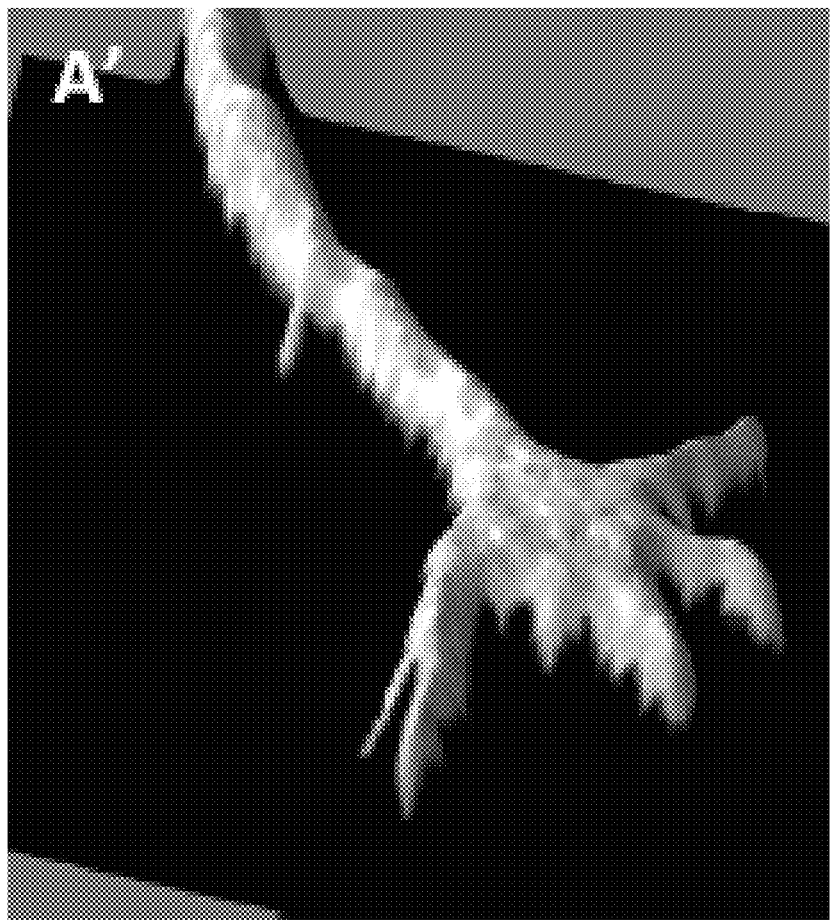

Once the parameters for depth assessment by PSF is determined, the sample blurred two-dimensional images are captured (111 in FIG. 1). FIG. 2C illustrates a captured two-dimensional image of a bright field image of a growth cone of cultured *Xenopus* spinal neurons, captured with a water immersion objective (60×, N.A. 1.1). The captured image (FIG. 2C) contains blurred portions. After denoising, a denoised, blurred two-dimensional image will be processed with deconvolution filtering (FIG. 1, 115) according to the PSF to generate a stack of deblurred two-dimensional images (FIG. 1, 117). Last, a three-dimensional image will be reconstructed from the deblurred two-dimensional image stack. In one embodiment, the three-dimensional image is constructed as known from the stacked series, similar as with confocal z-series images (121 in FIG. 1). FIG. 2D illustrates the generated three-dimensional image. Using this methodology, a three-dimensional image of fluorescent signals was successfully constructed from a fluorescent membrane potential indicator, Mermaid protein, in a cultured neuron growth cone (FIG. 4).

In one application of the described methods, in vivo three-dimensional images may be constructed. For example, three-dimensional images of the morphology of growth cones together with the fluorescent signals emanating from the Mermaid protein within them. Because the Mermaid protein is expected to be anchored at the plasma membrane, three-dimensional registry of Mermaid fluorescent signal will correspond that of the plasma membrane. The experiments could be performed similarly as reported (Nishiyama et al., Nat Cell Biol, 2011) except that entire spinal cords without fixation are used in the proposed study. Briefly, Mermaid protein is overexpressed in one side of *Xenopus* spinal cords by the microinjection of its mRNA into one dorsal blastomere of four-cell stage embryos. Animals are raised until stage 32 and spinal cords are isolated by removing surrounding skin, soft tissues and somites. Spinal cords will be placed on an agar plate in a lateral position with the side injected with the Mermaid mRNA facing the agar. In this configuration, growth cones of spinal commissural interneurons that migrate along the longitudinal axon tracts will face the objective lens. In the manner described above for calculation of depth according to PSF, a fluorescent bead, used as a z-axis reference, may be placed on the surface of the isolated spinal cord within the same visual field as the growth cones to be imaged. Finally, single, blurred fluorescent images of the commissural interneuron grow cones are captured and processed for three-dimensional image reconstruction.

As noted, using a 60× water immersion objective, three-dimensional images were successfully reconstructed of cultured commissural interneuron growth cones including their filopodial movements at a depth of up to ca. 10-µm from the focal level set at the surface of a coverslip. It is likely that with a 30× objective of similar N.A. as the 60× objective we will be able to reconstruct three-dimensional images at a distance of ca. 20-µm along a z-axis from single two-dimensional images that capture an entire growth cone.

Figure 7:
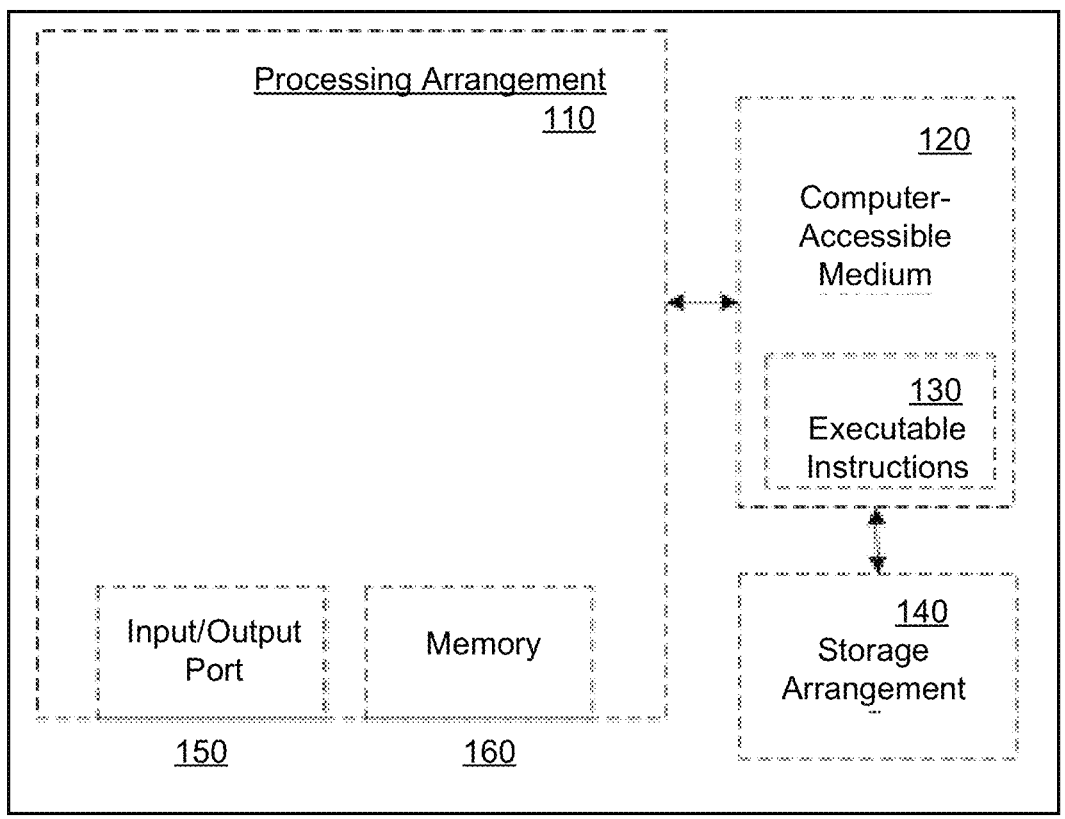
FIG. 7 illustrates an embodiment of a computer system of the present invention.

In one embodiment, shown in FIG. 7, a system 100 is provided for constructing a 3-dimensional image from a 2-dimensional image and compressing a 3-dimensional image to a 2-dimensional image. FIG. 7 shows an exemplary block diagram of an exemplary embodiment of a system 100 according to the present disclosure. For example, an exemplary procedure in accordance with the present disclosure can be performed by a processing arrangement 110 and/or a computing arrangement 110. Such processing/computing arrangement 110 can be, e.g., entirely or a part of, or include, but not limited to, a computer/processor that can include, e.g., one or more microprocessors, and use instructions stored on a computer-accessible medium (e.g., RAM, ROM, hard drive, or other storage device).

As shown in FIG. 7, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The computer-accessible medium 120 may be a non-transitory computer-accessible medium. The computer-accessible medium 120 can contain executable instructions 130 thereon. In addition or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example.

System 100 may also include a display or output device, an input device such as a key-board, mouse, touch screen or other input device, and may be connected to additional systems via a logical network. Input devices may also include an automated or manual microscope system that can be controlled by system 100. This automated or manual microscope system may be connected directly or via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps. In addition, the processes depicted in the accompanying figures do not necessarily require the particular order shown, or sequential order, to achieve desirable results. In certain implementations, multitasking and parallel processing may be advantageous.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above examples or may be acquired from future research of the disclosed embodiments. It is intended that the scope of the invention be defined by the claims appended hereto and their equivalents.

What is claimed:

1. A method for generating a three-dimensional image of an object, comprising:
   receiving a plurality of blurred two-dimensional images captured using an optic system;
   computationally generating, by a processor, a plurality of simulated blurred images corresponding to one of the plurality of blurred two-dimensional images, each of the plurality of simulated blurred images using a different standard deviation of a blur function distribution on the one of the plurality of blurred two-dimensional images, each standard deviation corresponding to a respective depth;
   determining, by a processor, a z-axis registry of a point spread function for the optic system, the determining comprising:
      using best fit parameters to minimize mean square error between the plurality of blurred two-dimensional images and the plurality of simulated blurred images to provide a depth estimation for a given blur of each of the plurality of simulated blurred images; and
      correlating each of the depth estimations to a magnitude of blur of each of the plurality of simulated blurred images and recording in the z-axis registry;
   receiving a blurred two-dimensional object image;
   deconvoluting, using a processor, the blurred two-dimensional object image using the point spread function for the optic system,
   to generate a stack of non-blurred two-dimensional images, each non-blurred image having a corresponding z-axis registry depth estimation; and
   constructing a three-dimensional image from the stack of two-dimensional images using the corresponding z-axis registry depth estimations.

2. The method of claim 1, wherein the generated stack of two-dimensional images contain only in-focus pixels.

3. The method of claim 2, wherein each non-blurred image contains only in-focus pixels of a z-axis coordinate associated with the non-blurred images, and wherein the z-axis coordinate is different for each of the non-blurred images.

4. The method of claim 1, further comprising capturing the plurality of blurred two-dimensional images by:
   capturing a reference image of a reference object under the optic system, the reference image having an associated z-coordinate;
   moving focal levels of the optic system along the z-axis; and
   capturing a second reference image having a second z-coordinate.

5. The method of claim 1, wherein the point spread function is based upon the best fit parameters.

6. The method of claim 1, further comprising denoising the blurred two-dimensional object image prior to deconvoluting.

7. The method of claim 1, wherein deconvoluting comprises detecting an edge of a target tissue.

8. A non-transitory computer-readable medium having instructions stored thereon, that when executed by a computing device cause the computing device to perform operations comprising:
   receiving a blurred two-dimensional image, the blurred two-dimensional image created by compressing a three-dimensional image;
   computationally generating, a plurality of simulated blurred images corresponding to the received blurred two-dimensional image, each of the plurality of simulated blurred images using a different standard deviation of a blur function distribution on the received blurred two-dimensional image, each standard deviation corresponding to a respective depth;
   receiving a z-axis registry, the registry correlating a depth estimation for a given amount of blur for each of the plurality of simulated blurred images;
   deconvoluting the blurred two-dimensional image using the z-axis registry to generate a stack of non-blurred two-dimensional images from the blurred two-dimensional image, each non-blurred image having a corresponding z-axis registry depth estimation; and
   constructing a three-dimensional image from the stack of non-blurred two-dimensional images using the corresponding z-axis registry depth estimations.

9. The non-transitory computer-readable medium of claim 8, wherein the generated stack of two-dimensional images contain only in-focus pixels.

10. The non-transitory computer-readable medium of claim 9, wherein each non-blurred image contains only in-focus pixels of the z-axis coordinate associated with the non-blurred images, and wherein the z-axis coordinate is different for each of the non-blurred images.

11. The non-transitory computer-readable medium of claim 8, wherein the operations further comprise generating the z-axis registry by:
   receiving a plurality of blurred two-dimensional images; and
   correlating a depth estimation to a magnitude of blur of each of the plurality of blurred two-dimensional images and recording in the z-axis registry.

12. The non-transitory computer-readable medium of claim 11, wherein a point spread function is based upon the correlation.

13. The non-transitory computer-readable medium of claim 8, wherein the operations further comprise denoising the blurred two-dimensional image prior to deconvoluting.

14. The non-transitory computer-readable medium of claim 9, wherein deconvoluting comprises an edge detection algorithm.

15. A system comprising:
   a processor configured to:
   receive a three-dimensional image;
   generate a stack of non-blurred two-dimensional images from the three-dimensional image, each non-blurred image having a corresponding z-axis coordinate;
   computationally generate a plurality of simulated blurred images corresponding to one of the plurality of non-blurred two-dimensional images, each of the plurality of simulated blurred images using a different standard deviation of a blur function distribution on the one of the plurality of non-blurred two-dimensional images, each standard deviation corresponding to a respective depth;
   computationally generate a z-axis registry, the registry correlating a depth estimation for a given amount of blur for each of the plurality of simulated blurred images; and
   convolute the plurality of two-dimensional images to a single two-dimensional image with blurred portions using the z-axis registry to determine each respective given amount of blur.

16. The system of claim 15, wherein the three-dimensional image was captured using an epi-fluorescence microscope.

17. The system of claim 15, wherein the generated stack of two-dimensional images contain only in-focus pixels.

18. The system of claim 16, wherein each non-blurred image contains only in-focus pixels of the corresponding z-axis coordinate and wherein the z-axis coordinate is different for each of the non-blurred images.

19. The system of claim 15, wherein the blur is Gaussian blur.

20. The system of claim 18, wherein a point spread function is based upon the correlation of each z-axis coordinate with a magnitude of blur.

* * * * *